United States Patent
Bennwik et al.

(10) Patent No.: US 6,730,066 B1
(45) Date of Patent: May 4, 2004

(54) LIQUID DELIVERY CONTAINER

(75) Inventors: Percy Bennwik, Saltsjö-Boo (SE);
Jonas Törnsten, Uppsala (SE)

(73) Assignee: Pharmacia AB, Stockholm (SE)

( * ) Notice: Subject to any disclaimer, the term of this patent is extended or adjusted under 35 U.S.C. 154(b) by 405 days.

(21) Appl. No.: 09/616,638

(22) Filed: Jul. 26, 2000

Related U.S. Application Data

(60) Provisional application No. 60/171,407, filed on Dec. 21, 1999.

(30) Foreign Application Priority Data

Aug. 3, 1999  (SE) ................................................. 9902832

(51) Int. Cl.⁷ ......................... A61M 35/00; B65D 35/22; B65D 35/28
(52) U.S. Cl. ............................. 604/296; 222/94; 222/95
(58) Field of Search ................................ 604/294–296; 222/94, 95, 105

(56) References Cited

U.S. PATENT DOCUMENTS

| | | | | |
|---|---|---|---|---|
| 1,751,341 A | * | 3/1930 | Leisse | 222/92 |
| 2,208,744 A | * | 7/1940 | Bergerioux | 222/105 |
| 2,642,062 A | * | 6/1953 | May | 604/68 |
| 2,649,995 A | * | 8/1953 | Muskin | 222/92 |
| 3,419,007 A | | 12/1968 | Love | |

(List continued on next page.)

FOREIGN PATENT DOCUMENTS

| | | | | |
|---|---|---|---|---|
| DE | 19500726 | 7/1996 | | |
| EP | 0129985 | 1/1985 | | |
| EP | 0139855 | 5/1985 | | |
| EP | 0224352 | 6/1987 | | |
| EP | 0469814 | 2/1992 | | |
| EP | 0 832 568 A2 | * | 4/1998 | A23G/9/28 |
| GB | 2242134 | 9/1991 | | |
| GB | 2246555 | 2/1992 | | |
| GB | 2255918 | 11/1992 | | |
| WO | WO9013328 | 11/1990 | | |
| WO | WO9600050 | 1/1996 | | |
| WO | WO9606581 | 3/1996 | | |
| WO | WO9704827 | 2/1997 | | |
| WO | WO9723177 | 7/1997 | | |
| WO | WO 01/08732 A1 | * | 2/2003 | A61M/11/00 |

*Primary Examiner*—Weilun Lo
*Assistant Examiner*—Michael Bogart
(74) *Attorney, Agent, or Firm*—Dinsmore & Shohl LLP

(57) ABSTRACT

Pressurisable container for storing and ejecting liquid, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid. The front wall is substantially rigid in relation to the rear wall, the rear wall before pressurizing the container is substantially flat or substantially single-curved and the rear wall is deformable under stretching to substantially fill out the container cavity. The invention also relates to methods for container manufacture and devices and methods for ejecting liquid from the containers.

83 Claims, 4 Drawing Sheets

U.S. PATENT DOCUMENTS

| | | |
|---|---|---|
| 4,072,249 A | 2/1978 | Ekenstam et al. |
| 4,090,642 A | 5/1978 | Baker |
| 4,216,881 A * | 8/1980 | Rosman ............... 222/94 |
| 4,236,516 A | 12/1980 | Nilson |
| 4,433,797 A | 2/1984 | Galia |
| 4,522,622 A | 6/1985 | Peery et al. |
| 4,627,432 A | 12/1986 | Newell et al. |
| 4,811,731 A | 3/1989 | Newell et al. |
| 4,952,212 A | 8/1990 | Booth et al. |
| 4,961,516 A * | 10/1990 | Nakamura ............... 222/94 |
| 5,026,343 A | 6/1991 | Holzer |
| 5,053,000 A | 10/1991 | Booth et al. |
| 5,207,217 A | 5/1993 | Cocozza et al. |
| 5,221,050 A | 6/1993 | Jeffries et al. |
| 5,349,947 A | 9/1994 | Newhouse et al. |
| 5,415,162 A | 5/1995 | Casper et al. |
| 5,425,480 A * | 6/1995 | Rabenau et al. ....... 222/153.07 |
| 5,429,280 A | 7/1995 | Bauer et al. |
| 5,497,763 A | 3/1996 | Lloyd et al. |
| 5,516,008 A | 5/1996 | Rabenau et al. |
| 5,622,166 A | 4/1997 | Eisele et al. |
| 5,709,202 A | 1/1998 | Lloyd et al. |
| 5,893,485 A * | 4/1999 | McGill ............... 222/95 |

\* cited by examiner

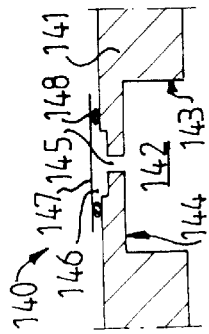
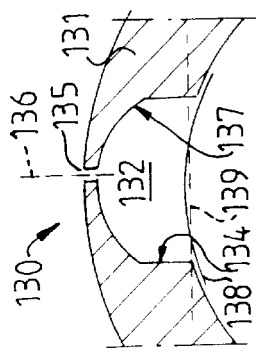
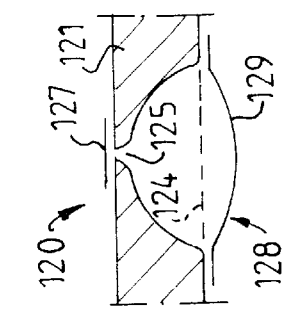
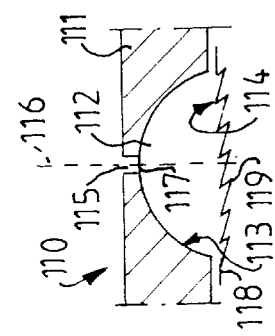
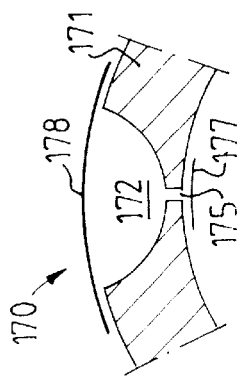
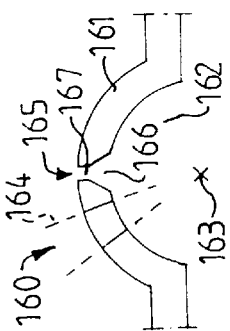
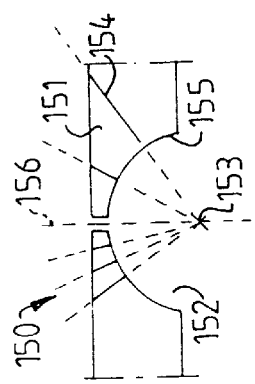

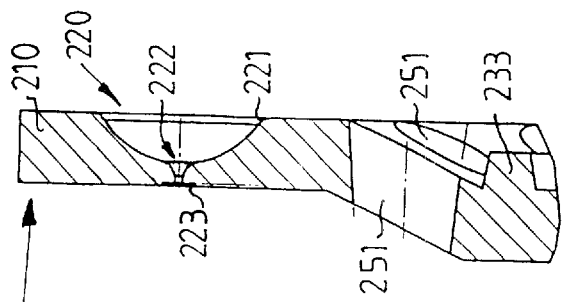
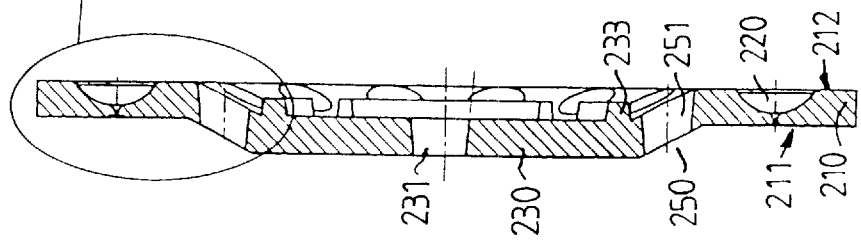
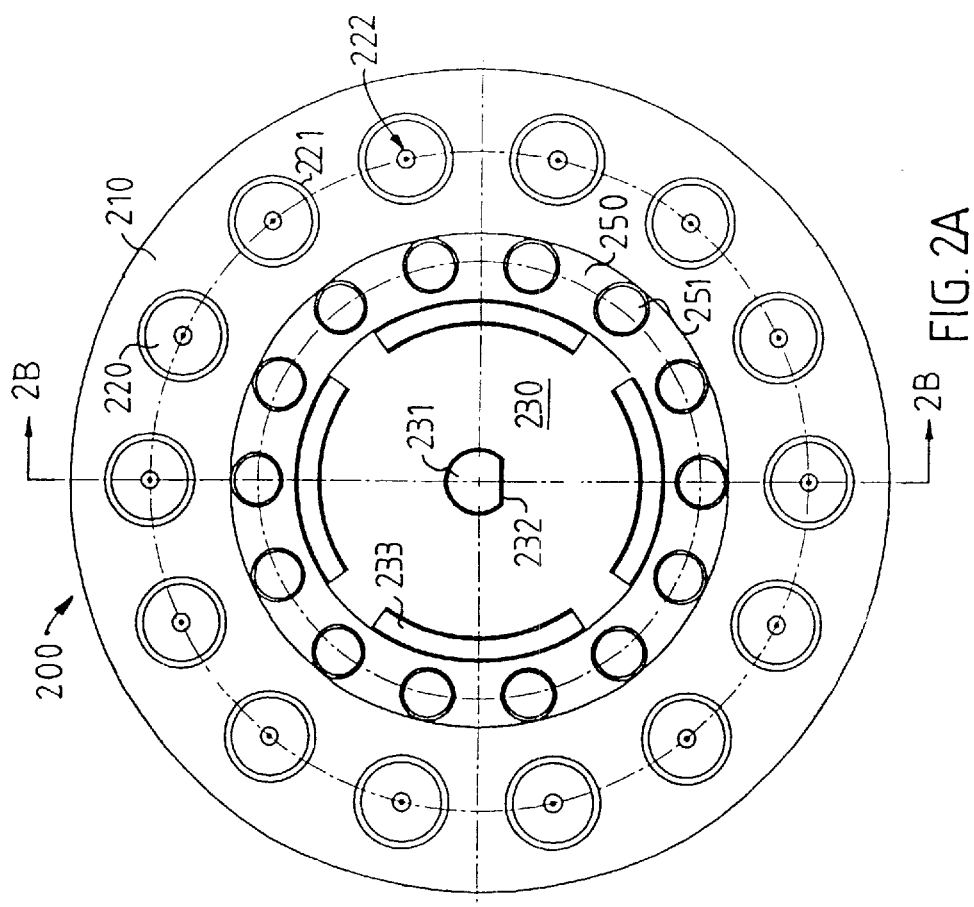

LIQUID DELIVERY CONTAINER

RELATED APPLICATION

The present application claims priority under 35 U.S.C. §119 of U.S. application Ser. No. 60/171,407, filed Dec. 21, 1999.

TECHNICAL FIELD

The present invention relates to Pressurisable containers for storing and ejecting liquid, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid. The invention also relates to methods for container manufacture and devices and methods for ejecting liquid from the containers.

BACKGROUND

Liquid containers designed not only to hold and store the liquid but also to deliver or expel the liquid tend to be growingly complex when the control demands on the delivery pattern increases. Whereas the complexity and expense, e.g. in pump systems, can be accepted under certain circumstances, such as in re-usable or multi-dosing devices, these conditions are not always present. It is for example often desirable to provide a single sealed container for each liquid dose to be delivered, e.g. to exactly control the dose and maintain sterility until the use moment in medical delivery applications, and under these unit dose circumstances the price restrictions becomes decisive. The design constraints may become still more severe with added requirements on delivery quality, e.g. in respect of delivery pressure, liquid speed, precise targeting, jet coherence, rapid stream rise and fall, fast delivery, small losses, precise dosing etc. High chamber pressures, e.g. to give high jet speeds or atomizing degrees, may counteract the cost aspect by requiring thick walls of special design or elaborate supports for the chamber or counteract the targeting by rupture, instability or dislocation of the opening. Jet coherence may require a precise opening channel inconsistent with minimum material and manufacturing conditions. High dosing precision requires complete chamber emptying and small losses, in turn requiring rapid pressure build up and fall, placing high demands on cavity stability and controlled collapse of the pressurizing wall. Secondary factors also need consideration. It is for example common to provide a temporary seal over the opening in order to fully seal the container before use and arrangements need to be present for rupture or removal of the seal in connection with delivery. Also, apart from the container properties as such, certain rigidity and additional structures may be needed for retaining the container in a delivery device fixture or seat. In order to avoid handling of individual unit dose containers it is also desirable to provide units of multiple connected containers for sequential firing in a dispenser device, which may require additional structural rigidity and features for feeding and stabilizing the individual containers in a device firing position. Manufacturing demands include both efficient production of the container parts as well as rational filling and sealing of the containers under high purity and even sterile conditions.

Prior art suggestions have met the abovesaid requirements only to a limited extent. The U.S. Pat. No. 4,090,642 describes a tape having multiple pockets for a flowable material and represents liquid dispensing with low delivery and control requirements since the flowable material is only to be squeezed out on the tape surface for contact application to the skin. The U.S. Pat. No. 5,497,763 specification relates to a system including a similar multiple dose tape for atomizing liquid to be inhaled. The delivery requirements are still low as atomization takes place with a separate vibrator and the demands on the tape reduce to liquid outflow through a porous membrane. The GB 2255918 specification similarly relates to droplet formation for inhalation purposes but liquid atomization here takes place by forcing the liquid through narrow container openings. In spite of the higher demands the proposed containers are separate collapsible containers or blister type sheets with multiple containers, requiring heavy support in the dispensing device when the pressure is applied to a dome shaped rear wall, the collapse of which cannot be fully controlled. It should also be noted that for the purposes described no liquid targeting is needed and no liquid stream formation since in connection with inhalation a mist of droplets is passively drawn into the lungs by the patient, even allowing redirection of the stream. The same applies for powder inhalers, as exemplified by WO 90/13328, GB 2242134, DE 19500726, WO 97/04827, U.S. Pat. No. 4,811,731, U.S. Pat. No. 5,207,217, U.S. Pat. No. 5,415,162, EP 469814, EP 129985 and U.S. Pat. No. 4,627,432, additionally different in that no atomization at all takes place and no discharge from nozzle type openings. Accordingly such demands are not considered and no container design suitable for such purposes is proposed. The WO 96/00050 and EP 224352 specifications do relate to the generation of a stream of droplets, actively shot and targeted towards an eye and able to traverse an air gap by own inertia. Typically, however, the dispenser arrangements required are elaborate and no suggestions are given for individual unit dose containers with integral delivery nozzles. The WO 96/06581 and 97/23177 specifications suggest such unit dose containers for similar eye treatment purposes. While meritorious in many respects the container designs proposed are similar to those already known and discussed, i.e. either elaborate separate containers or flexible bands with multiple blister type pockets having bulb type walls to be collapsed.

Accordingly there remains a need for improved integrated unit dose sealed container systems suitable both for liquid storage and liquid delivery under high control and quality demands.

SUMMARY OF INVENTION

A main object of the present invention is to avoid the abovesaid disadvantages of hitherto used container systems. A more specific object is to offer a unit dose sealed container system suitable both for liquid storage and liquid delivery under high control and quality demands. A further object is to provide such a system meeting high demands in respect of liquid speed, precise targeting, jet coherence, rapid stream rise and fall, fast delivery, small losses, precise dosing and/or complete container emptying. Another object is to offer a system allowing high chamber pressures with maintained container integrity and without rupture, instability or dislocation of the opening. Still another object is to offer a system allowing controlled collapse of the pressurizing wall. Yet another object is to offer a system useful for varying degrees of liquid stream momentum, e.g. characterized as low, moderate and high, allowing all from smooth application to penetrating strength. Another object is to offer system containers of low cost in material, component manufacture and filling. Still another object is to offer containers of high rigidity and stability. Yet another object is to provide such container designs suitable for multiple container units useful for sequential delivery of doses. Another object is to provide containers facilitating dispenser device design and requiring limited support at delivery. Another object is to provide a system easy to handle and convenient to operate for the end user.

These objects are reached with the characteristics set forth in the appended patent claims.

By use of a container sealing, collapsible, backing rear wall which before collapse have an overall planar or single-curved shape several precision related objects are reached. For each front wall overall shape the rear wall will have a minimum surface, giving volume and shape stability before collapse and a foreseeable and controlled collapse during pressurization of the container as no buckling, folding or crumpling of the wall is needed as in corresponding flattening or inversion wall deformations. A stretchable material in the wall will allow the wall to increase its surface during collapse, hereby avoiding rupture, permitting dynamic adaptation to any ram or hammer tool surface used for forced displacement of the wall and allowing the wall to conform to the opposite container cavity surface, all serving to give controlled pressure response, including initiation, continuation and fall, and precision in dosing and container emptying. Manufacturing advantages are reached among others in that the wall form facilitates its production, its sealing to the front wall in filling procedures and its joint attachment to several containers in multiple compartment units or packages. Handling, convenience and dispenser device design advantages are reached in that the initial wall shape may be used to give smooth rear wall surfaces and does not build on the boundaries of the material used for the vessel front wall design. Said front wall is relied upon for overall container static and dynamic rigidity. Contrary to blister type containers, the present vessel wall can be designed freely and needs not depend on the curvature of pressed structures for rigidity, can have a wall thickness at each location adapted to its functional object and needs not be locally weakened by stretch operations and can have an integral opening determined by design and not by manufacturing necessities. Wall stability is essential to volume control and the possibilities for consistent emptying. Wall and opening strength is essential to pressure resistance and the operative range of the system, reliable targeting and stable and coherent liquid jets. It also reduces the needs for extensive container support arrangements in the dispenser device and facilitates sequential feeding of containers into a shoot position. If the rigidity advantages are used to avoid bulb wall parts, dispenser container seat and feeding mechanism can be further simplified. Still the option is retained of providing multiple container units and is now not limited to tapes and other flexible structures but can with advantage be formed into self-bearing structures with improved handling and convenience characteristics, similar to that of individual containers. The vessel wall can for example be implemented as the resulting structure when forming the container cavity in an otherwise flat or single-curved plate, allowing both single and multiple container units of high structural rigidity and simple outer form, to the benefit of manufacture, dispenser design and end user handling, allowing free cavity designs e.g. for suitable flow characteristics and device head design as well as allowing opening designs of any length and form with high dynamic stability. Similar advantages are obtained if implemented with substantially constant vessel wall thickness or with increasing wall thickness when moving lateral out from the opening location of the wall. The vessel walls with opening in place can be manufactured as an integral, single material, structure e.g. by heat molding in common plastic tools, without need for stretch operations or separate nozzle forming steps, and are easily filled with liquid and sealed by the rear wall.

Further objects and advantages of the invention will be evident from the detailed description hereinbelow.

Definitions

As used herein the expression "single-curved" shall be understood as any form of a plane or surface obtainable from the same plane in flat form, without stretching or shrinking any part thereof in any direction within the plane, i.e. with maintained total surface for both the whole plane and any part thereof. In contrast, a "double-curved" plane or surface can only be obtained from a flat plane if deformed by stretching or shrinking. A curvature shall be regarded "continuous" if the change in curvature is constant or has a smooth variation and shall be regarded as "discontinuous" if there is a sharp change in the plane direction. As physical and non-limiting examples a cylinder surface or a corrugated surface are single curved as they can be formed from a non-elastic sheet, e.g. paper sheet, by pure bending whereas the surface of a sphere or saddle cannot be so formed without stretching and accordingly are double-curved. All these surfaces are continuous by having smooth curvature changes whereas for example a sheet with sharp folds are discontinuous at the fold lines.

As used herein "system" shall be understood to refer to the invention generally, when including its parts, such as the container and dispenser devices therefore, as well as methods for part operation and use.

In the absence of explicit statements to the contrary, as used herein expressions like "comprising", "including", "having", "with" and similar terminology shall not be understood to be exclusively restricted to recited element but shall be understood to allow for the presence of further elements as well and shall be understood to cover any element in integral, subdivided or aggregate forms. Similarly, expressions like "connected", "attached", "arranged", "applied", "between" and similar terminology shall not be understood to cover exclusively direct contact between the recited elements but shall be understood to allow for the presence of one or several intervening elements or structures. The same applies for similar expressions when used for description of forces and actions.

Also as used herein, positional and directional statements for both the container and the delivery device, such as "axial", "front" and "rear" and "forward" and "rearward", shall be understood with reference to the liquid delivery direction, with respect to which a line centered in the container opening and drawn along the main or average delivery direction shall be regarded as the system "axis" along which axis the liquid is delivered in the forward direction.

DETAILED DESCRIPTION

The container can be said roughly to include a front wall and a rear wall between which the container space, or enclosure, for the liquid is confined.

The container space is formed mainly between the front wall and the rear wall and includes a cavity part formed in, or surrounded by, the front wall. Although the space available for the liquid may be larger than the volume of the cavity proper, e.g. additional small volume in the opening and in a rearward protrusion or curvature of the rear wall, it is preferred that the cavity constitutes the major part of the space, especially when the rear wall in the preferred manner is substantially flat or single-curved. The cavity surface preferably has the shape of the space of a vessel, opening towards the rear wall and having its closed bottom toward the front wall. Among others in order to facilitate complete emptying and form adaptation between cavity and driving ram, it is preferred that the cavity has little, and preferably no, undercut parts when seen from the rear side. This may be accomplished with vessel surface parts being parallel with the cavity axis, e.g. cylindrical parts, but preferably the surface widens all the way from the axis and laterally outwards, to create a generally concave deepening when seen from the rear wall side. Although the surface may have sharp discontinuities, e.g. between an axial cylindrical surface and a more flat front part, it is preferred e.g. for rigidity reasons that the surface is substantially smooth and continuous. The cavity shape in cross-section planes perpendicular to the axis can have any shape, e.g. oval or polygonal, although preferably circular. Suitable overall forms are that of a dome or segment of a sphere. As known per se the space may be divided into two or more separate chambers, e.g. for sequential delivery or for mixing in connection with delivery, for example by use of interior walls running perpendicular or parallel with the axis. Such walls can be manually removable before actual delivery or may be rupturable in connection with delivery. Alternatively adjacent containers may contain different liquids and eject substantially simultaneously, either as two discrete jets or jets mixing in connection with ejection, e.g. by openings arranged offset and close to each other or directed towards each other.

The front wall is preferably more rigid than the rear wall, by comprising more rigid materials and/or material of thicker dimensions. For reasons outlined it is beneficial that the front wall provides the container and its opening with rigidity and stability and preferably the front wall alone is able to provide such rigidity, leaving the rear wall design free for other considerations. As long as these demands are met the front wall can have a variety of configurations. The front wall may have a roughly constant thickness when measured normal to the cavity surface, making the front wall shape about congruent with the cavity surface. It is preferred, however, that the wall thickness measured as stated has a variation and preferably so that the thickness increases when moving away from the axis. This gives the container as a whole a high targeting and pressure sustaining stability while allowing a short and low friction opening design. This in sharp contrast to blister type containers where stretch manufacture of the bulb results in weak lateral wall parts with low overall container stability. A preferred way of arranging for abovesaid variation in wall thickness is to make the front surface of the front wall substantially flat or single-curved, flat being most preferred, giving a lot of manufacturing and handling advantages as indicated. It is further preferred that also the rear surface of the front wall in the neighborhood of the cavity, and disregarding the form of the cavity proper, is single-curved and most preferably flat, giving similar manufacturing and handling advantages. Among others the flat or single-curved surfaces allow attachment thereto of originally flat sheets, films or foils without stretching thereof, e.g. a sealing film on the front surface and the backing rear wall on the rear surface of the front wall. Most preferably the front and rear surfaces are parallel or concentric respectively, giving e.g. overall plate or cylinder type structures, having good rigidity, handling and manufacturing properties.

The opening design can vary depending on the nature of the liquid stream to be produced, e.g. an atomized spray or a concentrated stream to remain coherent or to break up into a linear stream of discrete droplets. Also the stream speed may vary from high penetrating to low impact surface delivery. Several or multiple openings can be provided, e.g. to produce a controlled showed, although for most applications a single opening is preferred. The opening geometry can be that of a simple tube, diverging, e.g. for assisting in a distributed spray, converging, e.g. for assisting in a coherent stream to be formed, or a combination, such as a venturi type of channel. It is generally preferred to make the duct part of the opening short in order to keep the flow friction low. The desirable front wall thickness at the opening area can still be controlled, e.g. for rigidity purposes, e.g. by cutouts around the opening, preferably on the front surface of the front wall, also assisting in attaching a sealing film over the opening in a manner not interfering with the opening proper. The positioning of the opening with respect to the cavity can be asymmetrical, for example laterally offset towards the cavity side e.g. for mixing of adjacent jets, although normally it is preferred that the opening is symmetrically arranged with respect to the cavity, e.g. concentric with any cavity symmetry.

Although the above considerations apply to individual containers for single and discrete use it is preferred to provide for multiple container units or packages. This can be done by joining several individual container into multiple structures, e.g. by flexible joints to allow structures that can be bent, folded or rolled. Preferably, however, the multiple container package is a substantially rigid and self-bearing structure, among others giving advantages in connection with the delivery device. A rigid structure can be obtained by joining the individual containers by rigid joints but a preferred way is to utilize the rigidity of the front wall as described by providing an enlarged front wall structure and provide several cavities in the structure, among others facilitating manufacture of multiple containers and allowing a smooth and non-complicated exterior. By utilizing the feature of making the front and/or rear surface of the front wall structure flat or single-curved the attachment of films over these surfaces is further simplified, especially if the container surfaces lies in the same plane since an undivided sheet material can then be attached to several, and preferably all, of the individual containers of the structure, e.g. a common foil attached as rear wall to the rear surface of structure or a common peel sheet over the container openings at the front surface.

The overall shape of the front wall structure for multiple containers can take a variety of forms. A single-curved form for example can take the form of a partial or complete cylinder, allowing many containers on a limited volume and giving a very rigid structure. The container openings can be arranged on the cylinder exterior, e.g. if the dispenser device ram is arranged to hit from inner or concave side of the full or partial cylinder or if openings are provided diametrically opposite each rear wall for ram access therethrough from outside the cylinder. The container openings can be arranged on the cylinder interior, e.g. for simple exterior ram access to the rear wall and also in this case a diametrically opposite hole can be provided for passage of the liquid jet. Essentially flat front wall structures give advantages in manufacture and delivery device design. The shape may for example be rectangular, square or round. The round "disc" shape has been found particularly beneficial, among others in connection with the delivery device where sequential feeding of the containers into a shoot position can be made by simple rotation in a "revolver" type manner, the absence of any particular start position facilitates handling and counting arrangements and allows for self-centering properties.

The layout of the multiple containers on the available structure surface can be made in various ways. The containers can be arranged in a row or line, e.g. to avoid two dimension feeding. Alternatively several rows can be provided along several lines in two dimensions, e.g. parallel or concentric, to allow for a compact container arrangement.

The above design considerations for the front wall mainly apply to the parts occupied by containers, but other structures may be included for secondary purposes, e.g. for gripping, holding, centering or feeding discrete or multiple containers, in manufacture, in the delivery device and by the user, for adhering or removing sealing film etc. and these parts can be designed freely for their respective purposes.

The front wall is preferably made from suitable inert plastic materials such as polyethylene or polypropylene, possibly with reinforcing fillings of e.g. glass fibres, and can be manufactured in various ways, e.g. the cavities with opening can be made by machining in a raw material blank but the structures described can easily be formed in one step, e.g. by pressing although preferably by injection molding since all structures, including the opening, can be obtained with a dividable molding tool. Although the front wall can be made of a laminate or other composite material a single material is generally sufficient.

As said the rear wall serves the purposes of sealing the rear part of the container before ejection of the liquid and allowing collapse of the cavity during ejection. The rear wall should run at least partially perpendicularly relative the opening axis, i.e. forming a non-zero angle therebetween and preferably runs substantially perpendicularly thereto. The requirements on the rear wall material for scaling purposes depend on the particular application and liquid involved but generally it is desirable that the wall material is highly impermeable. It is also desirable to avoid solvents and other volatile components, both in the wall material and when attaching the rear wall to the font wall and preferably these parts are joined by heat sealing rather than by glue or adhesives. For the collapse purposes it is possible to have a rear wall material that breaks or ruptures when hit with the ram of the dispenser device, which, however, requires good sealing between ram and cavity. Hence it is preferred that the rear wall can be deformed without rupture, and most preferably be deformed to such an extent that it can fill out and conform to the inner surface of the cavity. The requirements for deformability can be reduced if the rear wall film is folded, e.g. in a continuous corrugated manner or in a discontinuous folded manner, i.e. in both cases with maintained single-curved shape, e.g. along single or multiple parallel lines over each container, to allow for unfolding as part of the deformation. In order to obtain a most controlled and reproducible collapse, however, it is preferred that no additional folds are used but that the rear wall when attached has substantially the same shape as the rear surface of the front wall. In any case the deformation during ejection will result in that the rear wall flat or single-curved shape is at least to some extent changed into a double-curved form, requiring some stretching of the material. The stretching and deformation can be elastic, as in a rubber sheet, e.g. if repeated use is intended, but is preferably at least partially and preferably substantially plastic in an irreversible manner, e.g. in order to avoid reuse of disposable containers or to prevent aspiration of air or liquid remains into the container after use. The rear wall preferably has the form of a sheet, film or foil of even thickness, which preferably is small compared to the front wall. The sheet may consist of a single material but preferably a composite material is used to meet all the requirements indicated. Most preferably the sheet is a laminate. Preferably the laminate comprises at least one impermeable and diffusion retarding layer, preferably a metal layer such as an aluminum layer, and at least one stretchable layer allowing deformation, preferably a plastic layer, e.g. of polyethylene, optionally also a heat sealable layer if the plastic layer does not have this property. In such a laminate it is acceptable that the metal layer breaks during wall collapse as long as remaining layers provide sufficient resilience for the deformation described.

As indicated it is preferred to temporary seal the container opening or openings before actual ejection of the liquid in order to maintain a fully sealed container. The seal should be broken or removed immediately before use. Although a manually or pressure breakable rupturable seal can be used it is often preferred to use a removable seal in order to avoid any particle release from the seal, to have a fully foreseeable dynamic behavior and allow use of more reliable thick or strong layers. Generally a seal can be formed integral with the front wall, e.g. by molding so as to leave a membrane of material somewhere in the opening duct. Preferably, however, a separate peel layer is provided for removal prior to ejection, and preferably attached to the front surface of the front wall. Again it is preferred to avoid glue and adhesives and preferably some form of welding is used, as by ultrasonic or heat. In order to facilitate removal and interference with the opening area the sealing can be made to a limited area surrounding the opening. In multiple container structures it is preferred to make the layers individually removable for each container, e.g. by use of separate films, pre-cut films or separate tongues, e.g. in a star shape for a round disc. For the film material similar considerations apply as for the rear wall material, although the film need not be deformable by stretching and the demands on impermeability can be slightly reduced in view of the small opening area.

The parts described should be joined and liquid filled into the cavity to form a prefilled sealed container, typically containing liquid for a single dose to be delivered. Although possible to fill the container cavity through the container opening, e.g. through a needle, the preferred way is to fill the cavity from the rear side of front wall before attachment of the rear wall. A useful procedure is then to adhere the sealing film over the opening or openings, possibly under welding action, filling liquid into the container cavity from the rear side and adhering the rear wall over the filled cavity, again possibly under welding action. Preferably these steps are made in the order mentioned. The invention contributes in several ways to the efficiency and simplicity of such a procedure, particularly in contrast to blister type manufacture and filling. In contrast to blister bulbs, flat sheets type materials can be used for the sealing film and the rear wall, allowing flat or single-curved adherence with equally simple flat or roll type tools and allowing adherence over several containers in multiple container structures and no stretch or other material deformation steps are necessary. Adapted welding action, e.g. heat, is applied individually to the sealing film and the rear wall respectively and directly to the adhering materials involved, whereas in blister manufacture sealing heat for front and rear materials has to be applied through a peel layer, over-adhering the peel layer, prolonging the process, possibly affecting the liquid present, and increasing product tolerances.

A delivery or dispenser device for ejection of the liquid from the containers can generally be said to comprise a housing with a seat for the container or container structure, a ram movable in relation to the housing in a direction substantially axial to the container when in the seat, an actuator arrangement operative to drive the ram.

The housing shall be understood in broad sense and may take a variety of forms. The device housing represents the point of reference for the container position and the movements described, such as the ram used for collapse of the container rear wall and for forces applied by actuating means performing said movements, whereat the force is applied between the housing and the moving part. The minimum functional requirement is that the housing offers a support or platform for the container and movable parts and the actuating means providing the movements and forces. As in common practice, however, it is preferred that the housing forms a container at least partly embracing the parts and preferably also to such an extent that only the features designed to be controlled or monitored by the operator are externally exposed, to give an overall convenient design to use.

The housing should contain a seat for a container or several containers, the minimum requirements on which is that at least the container to be emptied is kept fixed in relation to the ram, preferably so that the container axis and the movement axis for the ram are parallel and most preferably coaxial with respect to the ram part to hit the container rear wall. Preferably the seat should be able to accommodate containers with the characteristics described herein, e.g. with the shapes and sizes exemplified. The seat preferably supports the container against forward forces from the ram and preferably also against some rearward and lateral forces. The seat preferably allows the entire rear wall surface over the cavity to be exposed to the ram and should also expose at least the opening or openings on the front side of the container not to obstruct the liquid stream, although the rigidity of the present containers do not require any heavy support. Preferably the seat is also designed to allow easy exchange of discrete containers, or sequential movement of the individual containers of a multi-container structure, into the active position of the seat, e.g. by having a track in which the structure can be moved in one or two dimensions. In the preferred embodiment of containers placed in a circle, preferably on a disc shaped structure, it is suitable to rotate the disc around a central disc axis to bring the containers into alignment with the active position, in a revolver type manner. For single and in particular multiple container arrangements it is desirable that guiding arrangements are provided to secure good alignment with the ram axis in order to reach high delivery precision intended, e.g. structures provided in connection with each container on the package for cooperation with at least one corresponding locking structure on the housing, seat or preferably ram, arranged for interlocking at proper alignment. Locking therebetween can with preference be associated with a signal to assist stop in correct position, e.g. tactile or audible signal in manual operation or a mechanical or electronically detectable signal in automatic operation. Additionally it is preferred to include a counting arrangement, again manual or automatic, mechanical or electronical, designed to keep track on the number of containers used or remaining and warning for or preventing reuse of already emptied containers.

The ram may include a ram head and piston arrangement for moving the ram head along the movement axis. Although it is possible to design the ram head non-congruent with the container cavity, e.g. for use with different cavity shapes or when relying on rear wall stretch properties for emptying, it is preferred to design it for complete fill-out of the cavity. This can be done with a soft and adaptable ram head, e.g. for the purposes of being compatible with different cavity forms, to increase operation range or to obtain a certain emptying pattern, preferably to squeeze out the liquid from the peripheral cavity parts towards the central, axial, parts which can be done for example by making the soft ram head slightly shallower in shape than the shape of the cavity vessel form. For a single cavity form it is, however, preferred to make the ram head front surface substantially identical with the inner cavity surface or, expressed in another way, the rear surface of the front wall in the container space. The ram head can be surrounded by a support, e.g. a tube structure in which the ram head travels, which is preferably also abutted around the cavity to seal the space between ram head and cavity at least during the rear wall collapse movement, e.g. to allow high pressures or reduce leakage risks. The piston part of the ram is generally not critical to the dynamics of the ejection but rather for propulsion and will be described in connection with the actuator system.

The ram can be propelled by use of a variety of mechanisms and energy sources. The mechanism can be operated directly with manual energy, in which case, however, it is preferred to provide an leverage or gear exchange to amplify or transform force or speed, preferably towards lower speed and higher force. In order to have controlled and consistent results it is generally preferred to have automatic function in the sense that after operator triggering the propulsion takes place automatically, and preferably irreversibly, by use of stored energy. The energy may be stored in any way, e.g. in a mechanical spring, a gas spring or gas generator, as electrical energy or a combination thereof. The energy may be transmitted to the ram by suitable motor or transmission means, e.g. electric motor or solenoid type motor for electrical energy, a piston and cylinder arrangement for gas springs or gas generators and rotation axis or plunger for coiled and helical springs respectively. It is generally preferred to include a transmission between the motor means and the ram proper, among other to provide a force amplification, e.g. by use of a gear wheel or a cam surface type of transmission. It is preferred that at least the ram head, and preferably parts of the ram piston, are prevented from rotation during forward movement, which can be secured by any known guiding structures, such as a non rotation symmetric part cooperation with a complementary part, the parts being positioned on ram and housing respectively. A preferred transmission component for propulsion of the ram is a screw and nut arrangement, one of which is positioned on the ram and the other on the motor side of the transmission. The necessary speed, force and movement characteristics for the ram depends on a number of conditions, such as the nature of the container parts and opening, the particular application implementation, e.g. surface or penetrative delivery, the viscosity of the preparation, e.g. aqueous solutions or ointments, etc. and general statements cannot be given. However, the energy sources, motor means and transmissions exemplified can be adapted to each need. It has also been found beneficial to include a damper, e.g. a dash pot, a linear damper, a flow valve, a magnetic damper etc., to control speed with maintained stable force. In most applications it is desirable to have a rapid rise and fall of pressure, generally requiring a stable and non-retarded speed of the ram, which is facilitated e.g. by a damper or high inertia in ram and transmission.

It is also preferred to include in the device arrangements to facilitate breakage or removal of the temporary seal over the openings as described. Although it is possible to break a seal by the pressure itself generated when collapsing the rear wall it is preferred to use an active step to break the seal. This can be done by having a de-sealing tool arranged in connection with the housing, e.g. a penetrating tool for a rupturable sealing or a wedging or drawing arrangement for removal of peelable sealing films. Such arrangements can be located at or close to the seat, e.g. to allow late action, or remote, e.g. if the seat area is crowded. The de-sealing tool can be operated manually or automatically or compulsory, e.g. as a part of the movement of container into the seat site. It has been found beneficial, however, to position the de-sealing tool on the rear side of the container for movement from rear to front, which allows the de-sealing tool to attack the film in the best manner possible, i.e. on the film rear side to lift it from the front wall front surface. It also allows the de-sealing tool and mechanism to be arranged more conveniently within the housing and to the rear of the container for less interference with the ejection area and ejection target. The tool can have a movement mechanism of its own but most preferably the tool is arranged on or in connection with the ram in such a manner that it moves together with the ram, utilizing the same movement mechanism and facilitating a removal immediately before ejection and as an unavoidable part of the ejection procedure. Preferably the de-sealing tool passes though an opening in the front wall structure, and possibly also through the rear wall, at a location not occupied by the container cavity but covered by the sealing film. With preference the dimensions of such an opening and the de-sealing tool can be mutually adapted so as to act as a guiding arrangement, as described, for final alignment of ram and cavity before activation. In operation the tool first lifts the film from the container opening and the ram head then hits the container rear wall. It is possible to perform these two steps in a single continuous movement for the ram, e.g. for simplest operation and latest possible de-sealing, or in a two-step operation, possibly requiring two triggering actions from the user, e.g. in order to enable the user to verify that the film has been properly removed. It might also be of interest to use different movements characteristics for the two steps, e.g. a slow movement for the peel not to cause tearing or rupture and a fast action for ejection, which might require some shift arrangement, e.g. a gear shift, de-coupling of brake or damper etc. The general container design principles of the present invention strongly amplifies the above described advantages, among other by having a rigidity permittig front wall use for guiding purposes and allowing areas outside the cavity part to be utilized without instability problems.

Depending on each application it may also be beneficial to equip the device with means assisting targeting and positioning. For example, when used for shooting liquid to the eye the device front with a cowling, eye piece or eye cup for abutment to the eye socket. Penetrating applications may require small distance or direct contact between opening and target surface whereas larger surface treatment may require an end piece defining both an angle and a distance. As know per se for dispenser devices in general the device may also include mechanical or electronic warning, alerting or timing means.

As indicated in the introduction the invention described herein may be used for a variety of purposes within and beyond the medical area and for any type of preparations, such as chemicals, compositions or mixtures, in any container and delivered for any purpose. It may be used for liquids within a broad range of compositions, e.g. pure liquids, solutions, emulsions, dispersions, body fluids etc., and viscosities e.g. high viscosity ointments. For reasons outlined the system has certain special values in connection with medical delivery devices where also the design constraints are more severe than in most other applications. For convenience the invention has been described in terms of this application.

A preferred use of the invention is in connection with ophthalmic treatment of the eye with medical. The common administration manner is by eye drops or ointments, however, having several disadvantages. Both methods generally delivers a substantially higher amount than can be absorbed by the eye, not only resulting in dosing uncertainty and loss of expensive treatment medical but also in potential side-effects when non-absorbed preparation is drained away via the nasolacrimal duct, e.g. beta-blocking agents used in eye treatment has substantial systemic effects. Another problem is that the common administration methods tend to induce a blink reflex that may entirely destroy the treatment or at least introduce a high degree of uncertainty. Also the common methods do not provide an high degree of targeting precision, e.g. ability to hit the iris part of the eye being the penetrable part of the eye for prostaglandin. The principles used for the present invention solves these problems, among others by the possibility to deliver small amounts of liquid, actively ejected and not determined by liquid surface tension, by the possibility of delivering the liquid with sufficient speed to beat the blink reflex and by the possibility to eject a concentrated and coherent stream for precise targeting. Typical parameters for this application will be given below although the invention shall not be regarded as limited to any such exemplified parameter. A typical single dose volume for delivery to the eye can be less than 25 microliter, preferably less than 15 and most preferably less than 10 microliter. Generally the volume is at least 1, preferably at least 2 and most preferably at least 3 microliter. Since it is desirable that each container contains a single unit dose, these figures also relate to the liquid volume charged and contained in the containers, possibly allowing for some overfilling to compensate for non-ejectable amounts, such as liquid remaining as wetting film or in the container opening duct, e.g. 25% but preferably no more than 10% overfilling. In addition to the liquid the container may contain other material, notably gas such as air or a purging gas such as nitrogen or noble gases, e.g. to facilitate manufacture, assist in atomizing or act as pressure buffer, although in many instances little or no gas need to be present. The container can for example have a maximum cavity diameter is about 1 to 20 mm, preferably between 2 and 10 mm, calculated as a circle equivalent surface if the cavity is not round. A suitable speed for the stream of drops or jet ejected should be a balance between on one hand enough linear momentum to traverse an air gap between opening and target, without gravity assistance, and to travel fast enough not be obstructed by blinking and on the other hand not so fast as to cause inconvenient sensible impact on the eye. The ideal speed is to some extent dependent on the drop size used but as a general rule the drops should be able to traverse at least 1 cm, preferably at least 3 and most preferably at least 5 cm through air by own momentum, incorporating reasonable distances between opening and target. A suitable lower speed limit when leaving the opening is 1, m/s, preferably at least 5 m/s and most preferably at least 10 m/s. Generally the speed is lower than 200 m/s and preferably lower than 100 m/s. A suitable drop size so defined should be sufficient not to be retarded too quickly and not to be easily redirected, e.g.

to be inhaled, and preferably has a minimum diameter of 20 micron, preferably not less than 50 micron and most preferably at least 100 microns. Normally the size is less than 2000 micron and preferably less than 1500 micron. The stream may take the form of a shower or spray of atomized liquid droplets but preferably the stream is narrow and fairly coherent although even such a stream tend to break up into individual droplets after a certain time of distance. The above given values are intended to relate to spherical droplets and for multiple droplets to the weight average of particle diameters. A coherent stream tend to break up into droplets of a diameter of roughly double the diameter of the stream. Accordingly suitable opening diameters for the containers are about half the above given drop diameters or roughly between 10 and 1000 microns, preferably between 20 and 800 microns. A suitable front wall thickness, from front of opening to rear wall, may range from 0.5 mm to 10 mm and preferably between 1 and 5 mm. The above considerations are fairly independent of liquid viscosity and tend to apply both for solutions and ointments.

SUMMARY OF DRAWINGS

FIGS. 1A to 1G illustrates schematically in section various container designs and features useful in single or multiple container arrangements.

FIGS. 2A, 2B and 2C show in rear flat view, diametrical section and enlarged detail a multiple container structure in disc form, having 14 containers distributed around the disc periphery.

DESCRIPTION OF DRAWINGS

Figure 3A:
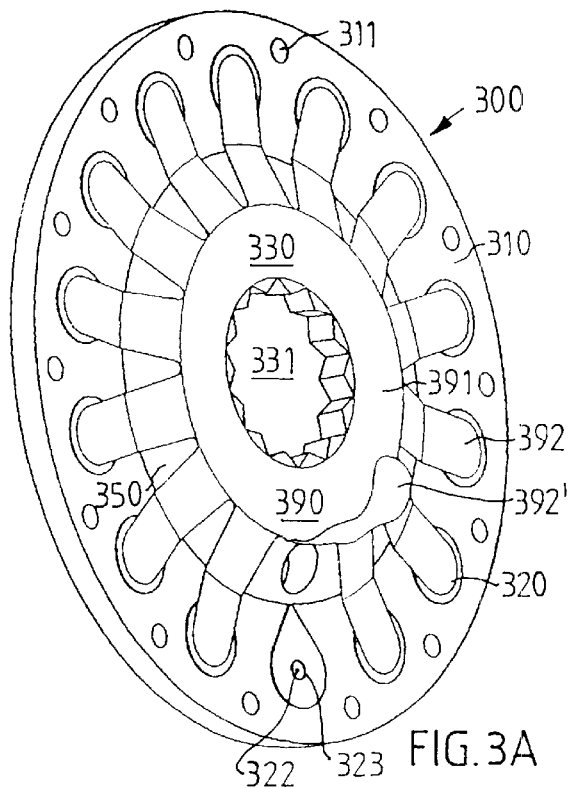
FIGS. 3A to 3D depicts a similar disc as in FIG. 2 in perspective views and partial sections, showing also rear wall and peel film.
Figure 3C:
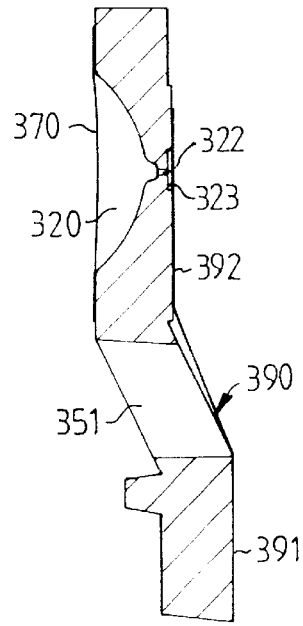
Figure 3B:
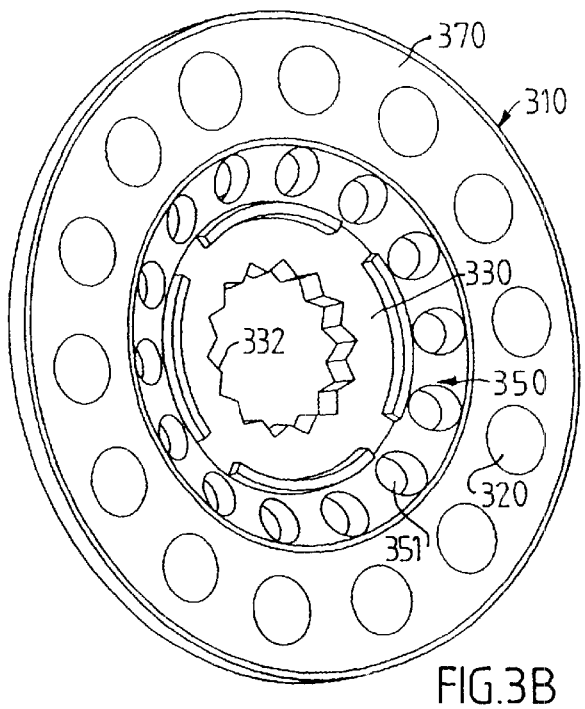

In FIG. 1 all embodiments, except that depicted in FIG. 1F, the front wall is formed from a plate type structure, being either flat as in FIGS. 1A, 1B, 1D and 1E or curved with concentric surfaces as in FIGS. 1C and 1G. The Figures illustrates various useful features but, for clarity, not all necessary or preferred details are shown in all Figures.

In FIG. 1A the container 110 comprises the front wall 111, having a front surface and a rear surface being substantially parallel. The front wall 111 has a cavity 112 in the form of a vessel with an front vessel surface 113 and an opposite rear opening 114. The cavity cross-section shown has the general form of a circle segment. An opening 115, defining a container axis 116, provides a fluid connection between the cavity interior and the exterior at the front wall front side. The opening 115 is here shown as a substantially constant cross-section channel with a thin inner membrane 117, formed from material left at injection molding and acting as a temporary seal to be broken at cavity pressurization. A deformable rear wall 118 covers the rear opening 114 of the cavity vessel with a seal (not shown). The rear wall is formed from an originally flat sheet material, here shown with discontinuous curvature in the form of a number of folds 119, running perpendicular to the Figure plane, the folds acting to reduce the necessary stretching of the rear wall material when forced into the container cavity.

FIG. 1B shows a container 120 similarly designed as in FIG. 1A except that the opening 125 is shown slightly convergent and is covered on the front wall front surface by a temporary seal in the form of a rupturable or peelable sheet 127, sealed to the front surface of the front wall. The rear wall 128 is here shown as a film with a continuous curvature part 129, providing an additional volume over that provided by the vessel when limited by the rear vessel opening 124, here illustrated with a dotted line flush with front wall rear surface, and also adding surface to the rear wall limiting stretching thereof. The curvature of rear wall part 129 can be formed from a flat sheet material if the curvature is constant normal to the Figure plane, as for a cylinder mantle surface, but need a double-curved material if in the form of a bulb.

FIG. 1C illustrates a container 130 formed in a front wall 131 basically in the form of a cylinder part with single-curved front and rear surfaces centered around a cylinder axis 133 and with an opening 135 on the cylinder exterior, convex, surface. Also illustrated is a cavity 132, having a cylindrical part 134 terminating in a sphere segment part 137, both parts symmetrically centered around opening 135 axis 136. Rear wall 138 is formed from a single-curved material continuously curved to adapt to the cylindrical inner surface of the front wall 131, hereby being larger in surface than a corresponding flat sheet over the cavity vessel opening, illustrated by dotted line 139.

FIG. 1D illustrates a container 140 with a front wall 141 having a cavity 142 the vessel surface of which has a cylindrical part 143 and a flat bottom part 144. Also illustrated is an opening 145 with a surrounding recess 146 on the front wall front surface, serving to avoid direct contact between the opening proper and a peel film 147 and its sealing surface 148, which is arranged in a ring outside the recess 146.

FIG. 1E schematically illustrates a container 150 with a cavity in the form of a circle segment, as in FIGS. 1A and 1B, centered around circle midpoint 153. Construction radii lines 154 drawn from point 153 intersects the inner surface 155 of the cavity 152 vessel perpendicularly and the Figure illustrates that the wall thickness, when measured along these construction lines normal to the vessel surface, increases (solid parts of lines 154) when moving laterally away from the cavity axis 156. In contrast, FIG. 1F illustrates a container 160 embodiment wherein the cavity 162 is formed in a front wall 161 design giving a constant wall thickness when measures along construction lines 164 centered in point 163 in the same manner as in FIG. 1E. This Figure also illustrates a longer opening 165 duct, having a convergent part 166 and a straight part 167 with roughly constant cross-section. For clarity, sectioning lines have been omitted in these Figures.

FIG. 1G illustrates a container 170 formed in a front wall 171 basically in the form of a cylinder part, as in FIG. 1C, with single-curved front and rear surfaces centered around a cylinder axis 173. However, in this embodiment the opening 175 is arranged on the cylinder interior, concave, surface. Rear wall 178 is formed from a single-curved material continuously curved to adapt to the cylindrical outer surface of the front wall 171, hereby again being larger in surface than a corresponding flat sheet over the cavity 172 vessel. Also a temporary seal film 177, covering the opening 175, is formed from a single-curved sheet material.

All container embodiments illustrated in FIGS. 1A to 1G can be used as single discrete containers or can be part of multiple container structures by being joined with similar or different container types, indicated by undefined lateral continuations of the front walls illustrated.

FIGS. 2A, 2B and 2C show in rear flat view, diametrical section and enlarged detail a multiple container front wall structure in disc form, having 14 containers distributed around the disc periphery. The disc, generally designated 200, can be said to include a peripheral front wall structure 210 with the containers, a slightly offset central auxiliary part 230 with actuating and holding arrangements and a transition part 250 with peeling and guiding arrangements. In the embodiment shown the plate like basic shape of the front wall structure 210 has a front side 211 and a rear side 212 and comprises 14 identical cavities 220 in the general form of circle segments, the rear rim 221 of which are slightly rounded. The cavity openings 222 are slightly convergent and on the front side 211 of the front wall structure 210 a small recess 223 is provided for reasons earlier outlined. The auxiliary part 230 can be said to include a central axis hole 231 for bearing and actuation purposes with a keying surface 232 providing non-rotational symmetry to facilitate actuation. The hole 231 preferably is slightly conical and converging from rear to front in order to facilitate actuator insertion and centering. Spacing ridges 233 serve to provide a gap between discs when stacked, e.g. in sterilization. The transition part 250 can be said to include bores 251, also slightly converging towards the front, serving to allow penetration of a de-sealing tool from the rear side towards the front side to lift off a temporary seal in the form of a peel film (not shown), the cooperation between the tool and the bore also acting as a guiding arrangement, centering the cavity with respect to a ram head of a dispenser device. With the cavity arrangement shown a flat rear wall film (not shown) can be positioned over the cavity rear sides to seal the containers, e.g. after filling. Each cavity can be sealed with individual film parts but it is also possible to use a single sheet for covering all cavities. Preferably such films are radially restricted to the front wall part 210 of the disc, leaving the transition part 250 and the auxiliary part 230 uncovered. A typical overall thickness of the front wall plate can be about 2 mm with a cavity depth of about 1.5 mm.

Figure 3D:
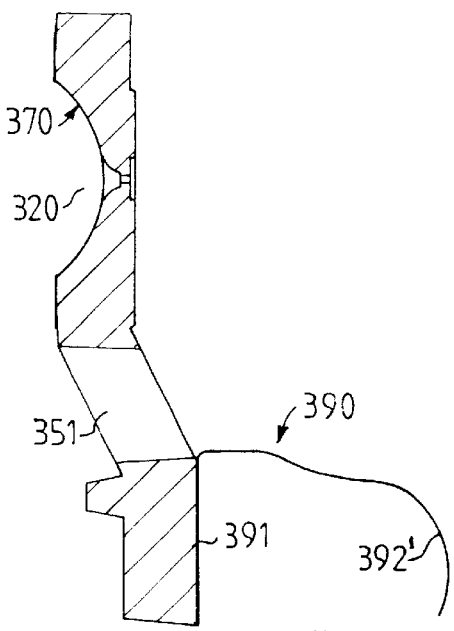

FIGS. 3A to 3D shows a similar disc arrangement as in FIG. 2. FIG. 3A is a perspective view of the disc front side, FIG. 3B a perspective view of the rear side, FIG. 3C a section from disc periphery to center through a cavity before ejection and FIG. 3D a similar section of the cavity after use. As in FIG. 2 the disc has a peripheral front wall structure 310 with the containers, a slightly laterally offset central auxiliary part 330 with actuating and holding arrangements and a transition part 350 with peeling and guiding arrangements. All details common with FIG. 2 will not be repeated. Also in this embodiment there are 14 identical cavities 320 in the general form of circle segments with cavity openings 322 with a front side recess 323. Holes 311 serves to facilitate handling of the disc, e.g. during manufacture and filling. The auxiliary part 330 here has a central axis hole 331 for bearing and actuation purposes with 14 symmetrically arranged teeth 332, allowing the disc to be attached to an correspondingly toothed actuating axis of a dispenser device without consideration to the positioning of any individual container or disc part. The transition part 350 has bores 351, serving to allow penetration of a de-sealing tool from the rear side towards the front side to lift off a temporary seal in the form of a peel film to be described. A single flat rear wall film 370, cut into ring form, radially restricted to the front wall structure 310, covers all the cavity rear sides to seal the containers. As best seen in FIG. 3A a peelable film 390 is attached to the disc front side so as to cover all cavity openings 322. The peel film is formed in star form from a single flat sheet and comprises a unifying central ring part 391, concentric attached to the auxiliary disc part 330, from which ring part tongues 392 radiate, one for each cavity, so as to pass over the transition part 350 under covering of the bores 351 and further radially out to cover the cavity openings 322. Initially all cavity openings 322 are covered by the tongues 392. When the liquid from one of the container is to be dispensed a de-sealing tool (not shown) is moved through the corresponding bore 351 from the disc rear side towards the front side, hereby lifting the corresponding tongue 392' to free and expose the corresponding cavity opening 322, as best seen in FIGS. 3A and 3D. The container content is then ejected by forcing the rear wall 370 under stretching from the flat condition shown in FIG. 3C to the cavity filling condition shown in FIG. 3D.

Figure 4A:
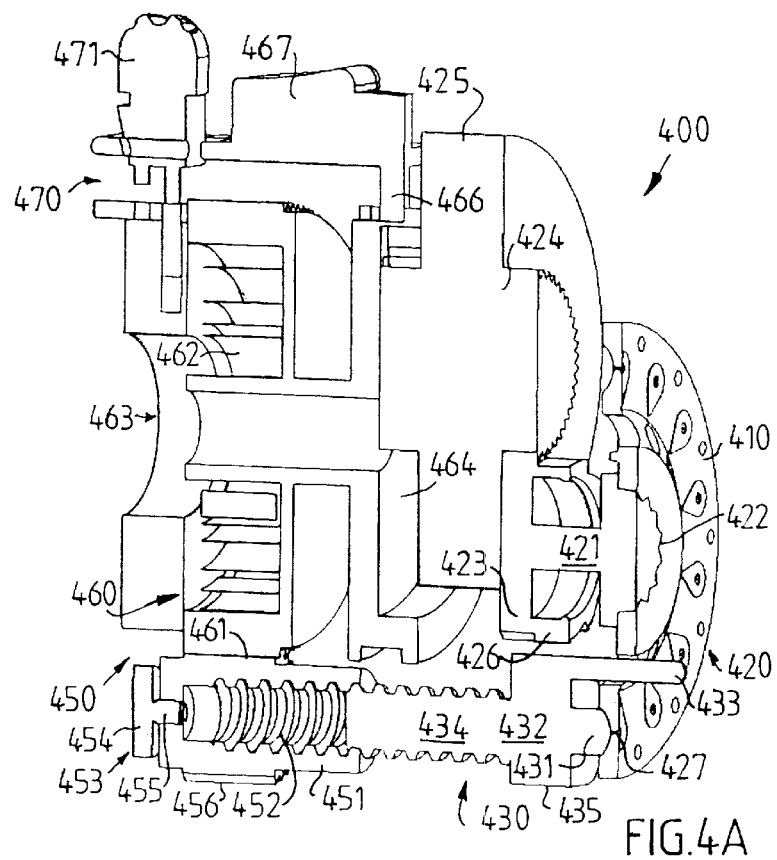
FIGS. 4A and 4B shows in partial section and perspective view respectively the internal parts of a dispeser device for disc type multiple containers.
Figure 4B:
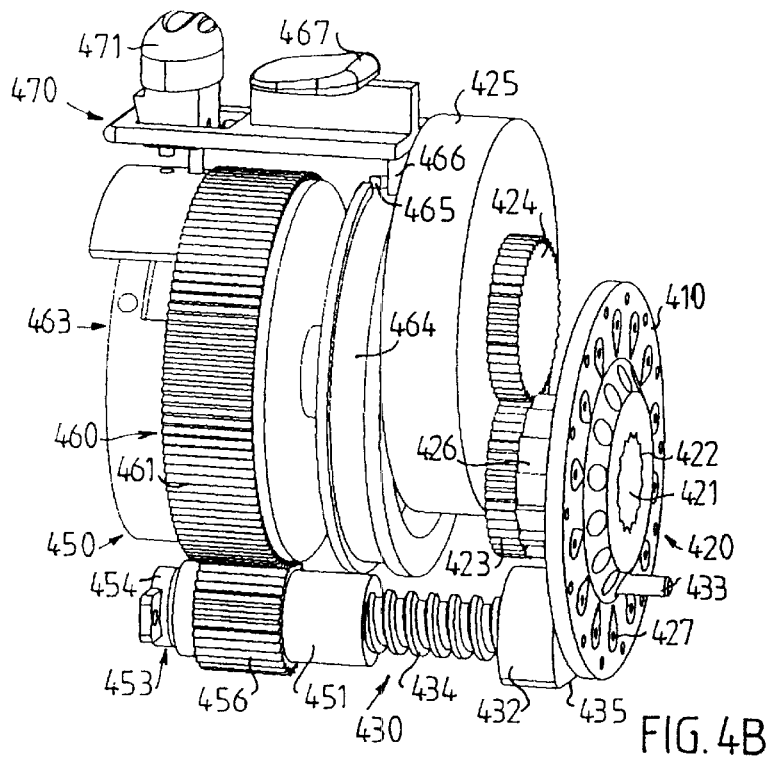

FIGS. 4A and 4B illustrates a dispenser device for multiple container discs as described in relation to FIG. 3. The device, generally designated 400, is shown without any casing part of the housing. The device receives the disc 410 at its front side, to the right in the drawings. The device can be said to include a seat 420 for the disc incorporating a disc bearing axis 421, having teeth 422 corresponding to the teeth of disc central opening. The axis 421 has a bearing gear wheel 423 cooperating with a control gear wheel 424 connected to a thumb wheel 425 for sequential advancement of the individual containers into the ejection position to be described. The thumb wheel can be actuated manually or a may be connected to a mechanism (not shown) for automatic incrementation in connection with the motor actuation cycle. A pawl and ratchet mechanism 426 secures that the disc occupies predetermined positions only and that it can be rotated in one direction only to avoid reuse of already emptied containers. These parts may also include counting means or other assistance (not shown) to urge for disc replacement. In the Figures the lowermost disc part is in the active ejection position 427 where the seat may comprise additional support or guidance (not shown) for the disc, e.g. to against forward and possibly rearward movement for example to balance force from the ram. Preferably such support structures can be arranged on a door arrangement of the housing for inserting the disc. In this position the cavity is centered with respect to the ram, generally designated 430. The ram includes a ram head 431 with a circle segment front form, adapted to the container cavity form. The ram head is part of a ram head support 432, also carrying a de-sealing and guiding tool in the form of a probe pin 433, arranged to penetrate bores, corresponding to the bores 351 in FIG. 3, in the disc 410 for the described purpose of lifting a temporary seal film from the container opening and of centering and stabilizing the container cavity with respect to the ram head 431. Probe pin 433 extends farther in the forward direction than ram head 431 in order to perform the above functions before the ram head hits the rear wall of the container. The ram further comprises an external screw-thread 434 for propelling the ram axially forwards and rearwards. The ram is keyed against rotational movements by guidance (not shown) of the ram head support 432 flat lower surface 435. The device further comprises a motor and transmission system, generally designated 450 for actuation of the ram movements. A rotationally arranged but axially stationary drive nut 451 has an internal screw-thread 452 for cooperation with ram external screw-thread 434 so as to move the ram axially at rotation of the drive nut. An angular viscous damper 453 has a stationary part 454 and a rotational part 455, connected to the drive nut 451 so as to rotate with the drive nut. The drive nut 451 has external gear teeth 456 by which the drive nut can be rotated. A rotationally arranged motor housing 460 has an external gear 461 of larger diameter than the drive nut 456. Inside motor housing 460 is arranged a motor spring 462, which can be cocked by rotation via a winding axis (not shown) entering trough the open part 463, to the left in the drawings, of the motor housing 460. Rigidly attached to the motor housing 460 and concentric therewith is a catch wheel 464 with a rim groove 465 for cooperation with an arming pin 466 of a manually accessible safety switch 467. A fire system 470 incorporates a release system (not shown) with a fire button 471 having two activation positions, a first partial operation of the fire button allowing the motor and transmission system 450 to advance the ram to move the probe pin 433 into to completed removal of the temporary seal film, but with no contact between container rear wall and ram head 431, and a second operation of the fire button 471 allowing the ram head 431 to complete its forward movement into the container cavity, as shown in the Figure. A typical propulsion speed for the ram during ejection can be for example about 2 mm movement performed during a time of about 50 msek, for a cavity depth of about 1.5 mm.

The invention is not limited to the embodiments described and exemplified but can be varied within the terms of the appended patent claims.

What is claimed is:

1. Pressurisable container for storing and ejecting liquid, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid, wherein the front wall is substantially rigid in relation to the rear wall, the rear wall before pressurizing the container is substantially flat or substantially single curved, and the rear wall is deformable under stretching to substantially fill out the container cavity.

2. The container of claim 1, wherein the cavity has the form of a generally concave deepening when seen from the rear wall side.

3. The container of claim 1, wherein the cavity has little or no undercut parts when seen from the rear side.

4. The container of claim 1, wherein the front wall has a roughly constant thickness when measured normal to the cavity surface towards the front wall.

5. The container of claim 1, wherein the front wall has thickness, as measured normal to the cavity surface towards the front wall, increasing in a direction away from the axis.

6. The container of claim 1, wherein the front surface of the front wall is substantially flat or substantially single-curved, at least in the area around the opening.

7. The container of claim 1, wherein the rear surface of the front wall is substantially single-curved, at least in the area around the cavity.

8. The container of claim 1, wherein the front and rear surfaces of the front wall adjacent the cavity are substantially parallel or concentric.

9. The container of claim 8, wherein the front wall has an overall shape of a plate or a cylinder part.

10. The container of claim 1, wherein the opening duct has a cross-section which is one of roughly constant, roughly converging, roughly diverging or a combination thereof.

11. The container of claim 1, wherein the opening is designed to assist in atomizing the liquid.

12. The container of claim 1, wherein the opening is designed to assist in forming a coherent linear liquid stream.

13. The container of claim 1, wherein the container is connected to at least one other container to form a multiple container unit.

14. The container of claim 13, wherein the front wall surfaces of several containers are arranged in the same flat or single-curved plane.

15. The container of claim 14, wherein the front wall surfaces of several containers are covered by a single sheet material.

16. The container of claim 13, wherein the rear wall surfaces of several containers are arranged in the same flat or single-curved plane.

17. The container of claim 16, wherein the rear wall surfaces of several containers are covered by a single sheet material.

18. The container of claim 13, wherein the unit is a substantially rigid and self-bearing structure.

19. The container of claim 18, wherein the unit comprises an enlarged front wall structure in which several cavities with openings are provided to form the multiple containers.

20. The container of claim 19, wherein the front and rear surfaces of the front wall structure are substantially parallel adjacent the cavities, to form a general plate form.

21. The container of claim 20, wherein the front wall structure has the overall shape of a disc.

22. The container of claim 20, wherein the several containers are positioned along at least one circle concentric with the disc periphery.

23. The container of claim 19, wherein the front and rear surfaces of the front wall structure are substantially single-curved and concentric adjacent the cavities.

24. The container of claim 23, wherein the front wall structure has the overall shape of a full or partial cylinder.

25. The container of claim 24, wherein the several containers are positioned over two dimensions of the cylinder surface.

26. The container of claim 1, wherein the rear wall is folded in a continuous or discontinuous manner.

27. The container of claim 1, wherein the rear wall has substantially the same overall shape as the rear surface of the front wall.

28. The container of claim 1, wherein the rear wall is designed to be deformed elastically.

29. The container of claim 1, wherein the rear wall is designed to be deformed inelastically or permanently.

30. The container of claim 1, wherein the rear wall comprises a laminate.

31. The container of claim 1, wherein the rear wall comprises a metal layer.

32. The container of claim 1, wherein a temporary sealing is provided over the opening.

33. The container of claim 32, wherein the sealing is rupturable or removable.

34. The container of claim 32, wherein the sealing comprises a flat or single-curved sheet.

35. The container of claim 1, wherein the liquid space volume is less than 25 microliter.

36. The container of claim 1, wherein the opening diameter is between 10 and 1000 micron.

37. The container of claim 1, wherein the front wall thickness is between 0.5 and 10 mm.

38. The container of claim 1, wherein the maximum cavity diameter is about 1 to 20 mm.

39. A kit or combination comprising a) a container according to claim 1 and b) a device having a ram arranged to displace or deform the container rear wall to pressurize the container liquid.

40. The container of claim 1, wherein the liquid space volume is less than 15 microliter.

41. The container of claim 1, wherein the liquid space volume is less than 10 microliter.

42. The container of claim 1, wherein the opening diameter is between 20 and 800 micron.

43. The container of claim 1, wherein the front wall thickness is between 1 and 5 mm.

44. The container of claim 1, wherein the maximum cavity diameter is between 2 and 10 mm.

45. Pressurisable container for storing and ejecting liquid, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid, wherein the front wall is substantially rigid in relation to the rear wall, the rear wall before pressurizing the container is substantially flat or substantially single curved, the rear wall is deformable under stretching to substantially fill out the container cavity, and the front wall front side has a cut-out area around the opening.

46. Pressurisable container for storing and ejecting liquid, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid, wherein in the vicinity of the cavity, the front wall has the overall shape, except for the cavity itself, of a flat or single-curved plate with substantially parallel or concentric front and rear surfaces, at least part of the cavity is formed between the front and rear surfaces with the opening exposed on the front surface and the open part of the vessel exposed on the rear surface, and the rear wall is attached to the rear surface.

47. Pressurisable container for storing and ejecting liquid, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid, wherein the front wall thickness, as measured along lines running through the cavity and normal to the vessel closed surface, increases in a direction off-set from the container axis.

48. A method for ejecting liquid from a container, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid, the method comprising pressurizing the container by moving the rear wall at least partially in the axial direction and towards the opening with sufficient speed to eject liquid through the opening and;

hereunder stretching the rear wall, elastically or inelastically, to increase its surface.

49. The method of claim 48, wherein the stretching step comprises the step of stretching the rear wall from a flat or single-curved form into a double-curved form.

50. The method of claim 48, wherein the stretching step comprises the step of deforming the rear wall until the rear wall is substantially corresponding to the cavity form.

51. The method of claim 48, wherein the liquid is substantially evacuated from the container.

52. The method of claim 48, wherein the liquid is ejected from the opening with a speed of at least 5 m/s.

53. The method of claim 48, wherein the liquid is ejected in the form of droplets of a diameter less than about 20 micron.

54. The method of claim 48, wherein the liquid is ejected in the form of a coherent jet.

55. The method of claim 48, wherein the liquid is allowed to pass through air a distance not less than 1 cm before hitting a target surface.

56. The method of claim 48, wherein the liquid is allowed to hit an eye.

57. The method of claim 48, wherein the liquid is allowed to hit a soft surface for at least partial penetration thereof.

58. A device for ejecting liquid from a container, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid and substantially fill out the container cavity, e) a housing with a seat for the container adapted to receive a container having a distance between rear wall and front wall front surface of at least 0.5 mm, f) a ram arranged in a moving direction, in relation to the housing, substantially axial to the container when in the seat, and g) an actuator operative to drive the ram.

59. The device of claim 58, wherein the container when in the seat exposes substantially the whole part of the rear wall surface covering the cavity towards the ram.

60. The device of claim 58, wherein the seat is arranged to allow exchange of containers in the seat.

61. The device of claim 60, wherein the seat is arranged to allow exchange by sequential feeding of containers in a multiple container unit into the seat.

62. The device of claim 61, wherein the seat comprises a track in which the containers can be fed.

63. The device of claim 61, wherein the seat allows sequential feeding by rotation of a multiple container unit having containers arranged in a circle pattern.

64. The device of claim 58, further comprising a guiding arrangement arranged to secure alignment between the ramp and the container cavity.

65. The device of claim 64, wherein the guiding arrangement comprises a releasable lock between the container and the housing or seat.

66. The device of claim 64, wherein the guiding arrangement is a releasable lock between the container and the ram.

67. The device of claim 66, wherein the lock comprises a structure locking the container when moved in the moving direction of the ram.

68. The device of claim 58, wherein the ram comprises a ram head and a ram piston.

69. The device of claim 68, wherein the front part of the ram head substantially conforms with the container cavity.

70. The device of claim 58, wherein the actuator comprises an electrical arrangement for driving the ram.

71. The device of claim 58, wherein the actuator comprises a mechanical arrangement for driving the ram.

72. The device of claim 71, wherein the mechanical arrangement comprises at least one spring for energy storage.

73. A device for ejecting liquid from a container, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid and substantially fill out the container cavity, e) a housing with a seat for the container adapted to receive a container having a distance between rear wall and front wall front surface of at least 0.5 mm, f) a ram arranged in a moving direction, in relation to the housing, substantially axial to the container when in the seat, comprising a ram head and a ram piston, and g) an actuator operative to drive the ram, wherein at least a front part of the ram head is made of a soft material adaptable to the container cavity.

74. The device of claim 68, wherein the actuator is arranged to displace the ram piston.

75. A device for ejecting liquid from a container, the container comprising a) a front wall having or surrounding a cavity corresponding to the form of an open vessel, b) an opening in the front wall adapted for election of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid and substantially fill out the container cavity, e) a housing with a seat for the container adapted to receive a container having a distance between rear wall and front wall front surface of at least 0.5 mm, f) a ram arranged in a moving direction, in relation to the housing, substantially axial to the container when in the seat, and g) an actuator operative to drive the ram, wherein the actuator comprises a transmission including at least one driving force transforming arrangement.

76. The device of claim 75, wherein the transmission includes a screw and nut arrangement.

77. A device for ejecting liquid from a container, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid and substantially fill out the container cavity, e) a housing with a seat for the container adapted to receive a container having a distance between rear wall and front wall front surface of at least 0.5 mm, f) a ram arranged in a moving direction, in relation to the housing, substantially axial to the container when in the seat, g) an actuator operative to drive the ram, and h) a damper arranged to affect the ram movement.

78. A device for ejecting liquid from a container, the container comprising a) a front wall having or surrounding a cavity corresponding to the form of an open vessel, b) an opening in the front wall adapted for ejection of the liquid from the container, said opening defining a container axis, c) optionally a sealing over the opening adapted for temporary use, and d) a rear wall closing and sealing the open part of the front wall vessel to confine a space for the liquid in the container, the rear wall running at least partially perpendicular to the container axis and being displaceable or deformable for movement towards the opening to pressurize the container liquid and substantially fill out the container cavity, e) a housing with a seat for the container adapted to receive a container having a distance between rear wall and front wall front surface of at least 0.5 mm, f) a ram arranged in a moving direction, in relation to the housing, substantially axial to the container when in the seat, g) an actuator operative to drive the ram, and h) a de-sealing tool arranged for breakage or removal of a sealing over the container opening.

79. The device of claim 78, wherein the tool is arranged to the rear of the container when in the seat and arranged for forward movement during de-sealing.

80. The device of claim 79, wherein the tool is arranged to pass through or past the front wall during its forward movement to attack the sealing.

81. The device of claim 80, wherein the tool and container are arranged to cooperate as a guiding arrangement arranged to secure alignment between the ram and the container activity.

82. The device of claim 79, wherein the tool is connected to the ram for common movement therewith.

83. The device of claim 82, wherein the tool is connected to the ram so as to hit the sealing before the ram hits the container.

* * * * *

UNITED STATES PATENT AND TRADEMARK OFFICE
CERTIFICATE OF CORRECTION

PATENT NO. : 6,730,066 B1
DATED : May 4, 2004
INVENTOR(S) : Percy Bennwik et al.

It is certified that error appears in the above-identified patent and that said Letters Patent is hereby corrected as shown below:

Column 17,
Line 63, delete "duct".

Signed and Sealed this

Fourteenth Day of September, 2004

JON W. DUDAS
*Director of the United States Patent and Trademark Office*